United States Patent [19]
Hennig et al.

[11] Patent Number: 5,431,638
[45] Date of Patent: Jul. 11, 1995

[54] ENERGY DISSIPATION DEVICE

[75] Inventors: Walter S. Hennig, Satellite Beach, Fla.; David T. Green, Westport, Conn.; Henry Bolanos, East Norwalk, Conn.; Daniel Shichman, Trumbull, Conn.; Charles E. Gorman, Hamden, Conn.

[73] Assignee: United States Surgical Corporation, Norwalk, Conn.

[21] Appl. No.: 80,264

[22] Filed: Jun. 21, 1993

Related U.S. Application Data

[63] Continuation-in-part of Ser. No. 683,253, Apr. 10, 1991, abandoned.

[51] Int. Cl.[6] .................... A61M 5/00; A61M 25/00
[52] U.S. Cl. ................... 604/264; 604/158; 604/165; 606/34; 606/35; 128/908
[58] Field of Search .................. 604/157–159, 604/164–165, 169, 184, 272–274, 264, 160; 174/47, 51; 606/32, 34, 35, 37, 39–41, 43, 44, 48–50; 128/908

[56] References Cited

U.S. PATENT DOCUMENTS

| | | |
|---|---|---|
| 3,070,132 | 12/1962 | Sheridan . |
| 3,580,983 | 5/1971 | Jackson .................... 174/47 |
| 3,834,392 | 9/1974 | Lampman et al. . |
| 3,963,856 | 6/1976 | Carlson et al. ............ 174/47 |
| 3,994,287 | 11/1976 | Turp et al. . |
| 4,184,492 | 1/1980 | Meinke et al. . |
| 4,601,710 | 7/1986 | Moll . |
| 4,744,361 | 5/1988 | Karasawa . |
| 4,886,505 | 12/1989 | Haynes et al. .......... 604/265 |
| 4,983,456 | 1/1991 | Iwaskow . |
| 5,009,643 | 4/1991 | Reich et al. ............. 604/165 |
| 5,116,353 | 5/1992 | Green . |
| 5,277,696 | 1/1994 | Hagen ...................... 606/50 |
| 5,295,979 | 3/1994 | DeLaurentis et al. ..... 604/265 |
| 5,295,993 | 3/1994 | Green ...................... 604/164 |

OTHER PUBLICATIONS

"Skin Burns from Electrosurgical Current," J. A. Pearce et al., *Medical Instrumentation*, vol. 17, No. 3, May–Jun. 1983 pp. 225–231.
"Materials Selector 1991," *Materials Engineering*, Dec. 1990 pp. 202–203, 214.
"Electrical Burns During Laparoscopy," *JAMA*, Dec. 17, 1973, vol. 226, No. 12, p. 1465.
"Principles & Hazards of Electrosurgery Including Laparoscopy," G. R. Neufield, *Surgery, Gynecology & Obstetrics*, Nov. 1978.
"A Method for Preventing Abdominal Burns Caused by Electrocautery During Laparoscopy," J. M. Esposito, *Am. J. Obstetr. Gynecol.*, vol. 114, No. 8, 1978, pp. 1105–1106.
"Endoscopic Applications of Electrosurgery: A Review of Basic Principles," D. E. Barlow, *Gastrointestinal Endoscopy*, vol. 28, No. 2, 1982, pp. 73–76.
"Safeguards in Laparoscopy: Education, Equipment Care, and Electron Control," R. M. Soderstrom, *Contemporary OB/GYN*, vol. 11, Mar. 1978, pp. 95–107.
"High Frequency Currents in Endoscopy: A Review of Principles and Precautions", L. E. Curtiss, *Gastrointestinal Endoscopy*, vol. 20, No. 1, 1973, pp. 9–12.
Valleylab SSE2L Instruction Manual, Aug. 1, 1984.
"Danger! Electrosurgical Units at Work," *Health Devices*, Jun.–Jul. 1973, pp. 218–226.

*Primary Examiner*—Randall L. Green
*Assistant Examiner*—P. Zuttarelli

[57] ABSTRACT

An accessory device for dissipating electrical energy from a surgical device is provided. The electrical energy is induced on the surgical device when a charge-inducing instrument, e.g. an unipolar electrocautery device, is energized in proximity thereto. The induced energy is dissipated by conveying the energy along an electrically conductive coating adhered to a housing of the device to an energy dissipation region.

18 Claims, 7 Drawing Sheets

ENERGY DISSIPATION DEVICE

CROSS-REFERENCE TO RELATED APPLICATIONS

This is a continuation-in-part of U.S. application Ser. No. 07/683,253 filed Apr. 10, 1991, now abandoned which is hereby incorporated by reference in its entirety.

BACKGROUND OF THE INVENTION

1. Technical Field

The present invention relates to a device and method for dissipating electrical energy during a surgical procedure and, more particularly, to an energy dissipation device and method having application in endoscopic surgical procedures.

2. Description of the Related Art

Endoscopic procedures have been practiced for many years. Initially, endoscopic procedures were primarily diagnostic in nature, i.e., involving the introduction of laparoscopes and like devices to view internal organs. Laparoscopic sterilizations have also been performed for some time. More recently, surgeons have begun to perform complex and innovative endoscopic surgical procedures. For example, endoscopic cholecystectomy has become a preferred modality for gall bladder removal in just the last two years.

Endoscopic procedures are typically performed through trocar sleeves or cannulas. Prior to introducing the cannula through the body wall, the surgeon generally insufflates the body cavity with carbon dioxide, e.g., through a Verres needle or like device. Insufflation creates a free area between internal body organs and the body wall. The surgeon then introduces one or more trocars through the body wall into the insufflated body cavity.

Trocars are sharp pointed instruments which include a trocar shaft or obturator with a piercing tip located at the distal end thereof. The trocar is positioned within a cannula for introduction of both into the body cavity. After introduction, the trocar is removed from the cannula and endoscopic instrumentation may be introduced through the cannula to effect diagnostic and/or surgical procedures. The cannula is typically provided with an internal flapper or trumpet valve to prevent gas release from the body cavity and generally measures from 3 to 12 mm in diameter. Safety trocars which include a spring-loaded safety shield surrounding the obturator are also known. See U.S. Pat. No. 4,601,710 to Moll et at.

A wide range of accessory instrumentation finds application in endoscopic surgical procedures. For example, graspers, dissectors, clip appliers, lasers and electrocautery devices are routinely employed. It is also common to perform a cholangiogram by introducing a catheter into the cystic duct during an endoscopic cholecystectomy. To obtain high quality imaging, radiolucent (rather than stainless steel) cannulas are typically employed in the region of the cholangiogram. Tissue gripping devices have also been developed for deployment on the exterior of the cannula, either permanently or removably, to prevent the cannula from working out of the body wall as a result of instrument manipulation therethrough.

Surgeons have long employed cautery to destroy or vaporize tissue and to cut and coagulate vessels and tissue through the application of electricity, heat or corrosive chemicals. Electrocautery (or galvanocautery) is routinely used to achieve hemostasis, both in endoscopic (closed) and non-endoscopic (open) surgical procedures. Electrocautery operates by taking advantage of the resistance to the flow of electrical current through tissue, such resistance resulting in heat generation as current attempts to pass therethrough. The degree of resistance to electrical current flow for tissue depends primarily on its vascularity and water content, with bone and fat having a higher resistance to current flow than skin and muscle.

Electrocautery instrumentation is typically either unipolar or bipolar. In unipolar applications, electrical energy is supplied from a generator to the end of an electrical conductor, e.g., cauterization wire, which is pressed against or placed adjacent the desired surgical site. A grounding plate is typically located below the patient so that the electrical current delivered by the cauterization wire passes through the patient to the plate, thereby completing the electrocautery circuit. In bipolar electrocautery, by contrast, a grounding wire is pan of the instrumentation placed adjacent the surgical site and the electrical current passes directly from the cauterization wire, through the tissue at the surgical site, and to the grounding wire.

Electrical burns constitute the most common electrical hazard in the operating room, the majority of which are associated with the use of electrosurgery or cautery units. A radio frequency generator supplies alternating current to the active electrode tip at frequencies between 300 thousand and 2 million hertz (cycles/second). Higher frequency devices are preferred to minimize the likelihood of muscle and nerve stimulation, i.e. electrical shock. The total power output of such units typically ranges from 40 to 600 watts and the units supply up to 10,000 volts. The current density at the tip of the electrode is extremely high, allowing the surgeon to achieve local heating and coagulation. To minimize the risk of extraneous burns in endoscopic procedures, it has been suggested that low power electrosurgical units and bipolar gasping forceps be employed and that insulation of accessory instrumentation, the cannula and the laparoscope be undertaken. See "Principles and Hazards of Electrosurgery Including Laparoscopy," G. R. Neufield, *Surgery, Gynecology & Obstetrics*, November 1978.

It has been reported that conductive trocar sleeves (or cannulas) can result in internal bums, particularly where the operative portion of the electrocautery instrument is not advanced beyond the end of the cannula. The suggested solution to this risk is the use of non-conductive cannulas, e.g., by placing a polyolefin heat-shrinkable tubing on the exterior of a conductive, stainless steel cannula. See "A Method for Preventing Abdominal Bums Caused by Electrocautery during Laparoscopy," J. M. Esposito, *Am. J. Obstetr. Gynecol.*, Vol. 114, No. 8, 1972, pages 1105–06.

It has also been reported that endoscopic use of electrocautery devices can induce an electrical charge in or on the endoscope through which the electrocautery device is operated, despite the insulation of the electrocautery device. It will thus appear that high frequency current is leaking through the insulation, when in fact no electrons are passing therethrough. This phenomenon has been described as "capacitive coupling." See "Endoscopic Applications of Electrosurgery: A Review of Basic Principles," D. E. Barlow, *Gastrointesti-* nal *Endoscopy*, Vol. 28, No. 2, 1982, pages 73-76; "Safeguards in Laparoscopy: Education, Equipment Care, and Electron Control," R. M. Soderstrom, *Contemporary OB/GYN*, Vol. 11, March 1978, pages 95-107.

The induction of electric charge has also been observed on the surface of nonconductive cannulas when used endoscopically with a unipolar cautery. The electrons passing through the unipolar cautery create an electromagnetic field which in turn creates an electric charge in the nearby cannula. The electric charge thus created is proportional to the frequency of the energy supplied to the cautery device. This electrical charge may be stored and released through a small area, such as the cannula touching the bowel, resulting in a burn. An electromagnetic field is not generally created when a bipolar cautery is used because electric currents run in both directions within the cannula, so that the net electromagnetic field is zero. In the case of unipolar cautery, unless this electrical energy is dissipated, contact between the "charged" cannula and an internal body organ or viscera may burn the organ or viscera.

Thus, means are needed to ensure that any electrical energy induced in or in any way conveyed on to surrounding structures by the use of electrosurgical devices is controllably dissipated in a safe manner.

SUMMARY OF THE INVENTION

In accordance with the present invention, a surgical device is provided which is adapted to dissipate electrical energy induced during a surgical procedure, e.g., through the endoscopic use of an electrocautery instrument. The surgical device of the present invention includes:

(a) a tubular member defining a longitudinal axis adapted to receive an electrical charge-inducing element, the tubular member being fabricated from a substantially dielectric material;

(b) electrical conductive means associated with the tubular member for conducting induced electrical charge along the longitudinal axis of the tubular member, and (c) energy dissipation means communicating electrically with the electrical conductive means, the energy dissipation means facilitating grounding of the tubular member.

In a preferred embodiment of the invention, the tubular member comprises a cannula fabricated from a substantially dielectric, i.e., substantially non-electrically conductive, material such as fiberglass. Suitable electrical conductive means include one or more conductive wires embedded within, e.g. by insert molding, or mounted to the interior and/or exterior surfaces of the tubular member, electrically conductive materials interspersed within the tubular member, e.g., metal or carbon fiber particles, or an electrically conductive coating or surface treatment, e.g. a conductive ink or a surface deposition of aluminum or like material.

The electrical conductive means is adapted to convey electrical energy to a region remote from internal body organs where electrical grounding may be safely and efficiently accomplished. For example, an electrically conductive band may extend around the periphery of the tubular member, thereby forming an energy dissipation region. Preferably, the energy dissipation region is configured and dimensioned to provide a relatively large grounding surface area, thereby minimizing current density. A preferred mechanism for energy dissipation involves positioning the energy dissipation region so as to communicate electrically with the body wall of the patient. In this way, the tubular member may be continually grounded by the patient without risking electrical energy build-up in or on the tubular member and burn injury to internal organs.

It has also been found according to the present invention that an improved accessory surgical device may be provided which includes:

(a) a housing fabricated from a substantially dielectric material and adapted to be mounted to the exterior of a tubular member, the tubular member defining a longitudinal axis and being adapted to receive an electrical charge-inducing element;

(b) electrical conductive means associated with the housing for conducting an induced electrical charge longitudinally along said housing; and (c) energy dissipation means communicating electrically with the electrical conductive means, the energy dissipation means facilitating grounding of the housing.

In yet another embodiment of the invention, an improved accessory surgical device may be provided with an electrical conductive coating. The electrical conductive coating enables enhanced conduction and dissipation of induced electrical charge along the exterior portion of the accessory surgical device.

In particular, the improved accessory surgical device includes a housing configured to be adapted to the exterior of a cannula, with the housing being preferably formed of a dielectric material. The housing defines a longitudinal axis and the cannula/housing combination are adapted to receive an electrical charge-inducing element. Preferably, the exterior of the longitudinal axis of the housing is provided with an electrical conductive coating which consists of copper, nickel and chrome. In addition, the electrical conductive coating preferably extends around the distal end of the housing and onto the interior of the housing. The interior coating facilitates electrical contact with the cannula to which the housing is mounted.

The electrical conductive coating facilitates the conduction of induced electrical charge which accumulates along the exterior of the longitudinal axis of the housing and/or which is present in or on the cannula, e.g., through capacitive coupling or charge leakage. Energy dissipation means may be provided in electrical communication with the electrical conductive coating to enable the induced electrical energy to be dissipated into either the body wall of the patient or to an external grounding mechanism.

Illustrative of the improved accessory devices of the present invention is a guide tube positioning device of the type disclosed in commonly assigned U.S. Ser. No. 07/489,482, the contents of which are hereby incorporated by reference. Such an accessory device may be removably secured to an electrically conductive, e.g., stainless steel, cannula. The electrical conductive means is adapted to convey induced energy from the cannula across the housing to energy dissipation means where grounding is accomplished. The accessory device may also form a distally-extending part of the cannula housing to which the cannula is mounted. In any case, the accessory device permits energy transfer to an energy dissipation region, thereby greatly minimizing the risk of burn injury to internal organs through contact with an energized cannula.

Further features of the subject invention will become more readily apparent from the following detailed description of the invention taken in conjunction with the accompanying drawings.

DETAILED DESCRIPTION OF THE INVENTION

Figure 1:
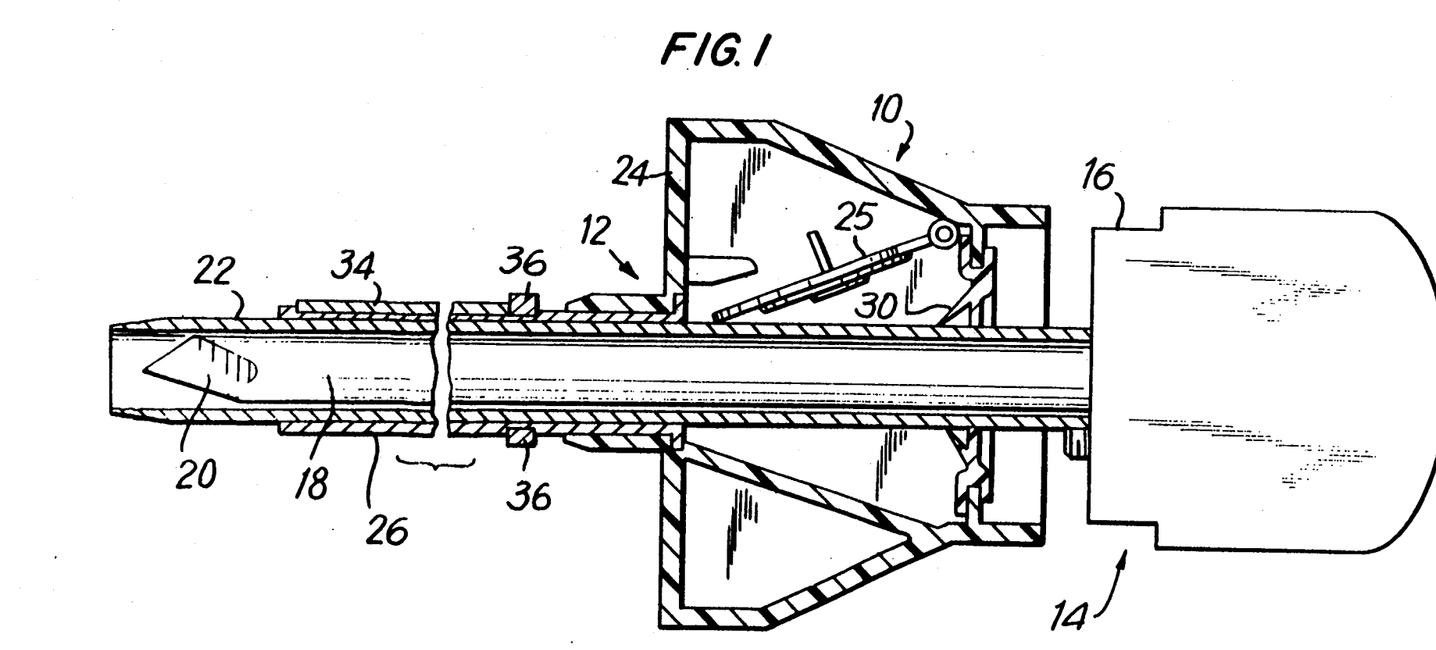
FIG. 1 is a top view, partially in section, of a trocar of the present invention, the trocar including a cannula assembly and an obturator assembly.
Figure 2:
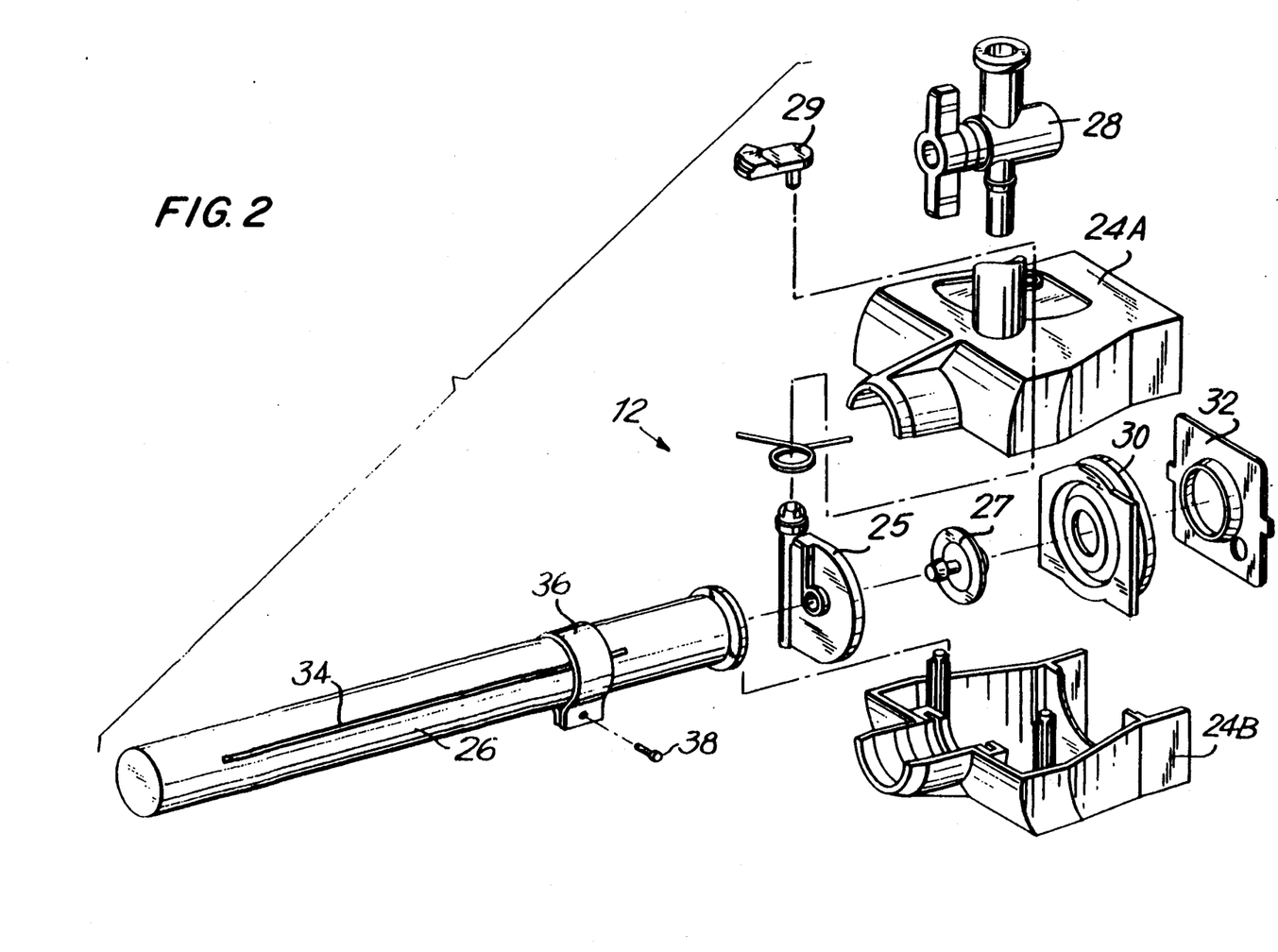
FIG. 2 is an exploded view of a cannula assembly.

Referring to FIGS. 1 and 2, trocar 10 includes a cannula assembly 12 and an obturator assembly 14. Obturator assembly 14 comprises an obturator housing 16, obturator shaft 18 with a pyramidal piercing tip 20 at its distal end, and a spring-loaded tubular element 22 which shields piercing tip 20 in its spring-biased distal position.

Cannula assembly 12 includes a cannula housing 24 (formed by top and bottom portions 24A and 24B, respectively) in which is pivotally mounted a flapper valve 25, and a cannula 26. Torsion spring 23 biases flapper valve 25 into engagement with gasket 30. Insufflation lever 29 permits manual manipulation of flapper valve 25. A stopcock 28 is mounted to cannula housing 24 to permit gas insufflation and desufflation through cannula assembly 12. A stabilizer plate 32 is mounted within cannula housing 24 proximal of gasket 30 which cooperates with proximally-facing valve member 27 of flapper valve 25 and accessory instrumentation (not pictured) introduced therethrough to provide a gas seal.

Cannula assembly 12 is sized to receive obturator shaft 18 and tubular element 22 longitudinally therewithin. Thus, as shown in FIG. 1, tubular element 22 and obturator shaft 18, which form a subassembly, are removably received within cannula 26 and extend longitudinally therebeyond. When pressed against a body wall, tubular element 22 reciprocates proximally to expose piercing tip 20. Once the piercing tip enters the body cavity, tubular element 22 springs forward to shield piercing tip 20, thereby minimizing the likelihood of inadvertent injury to internal organs. It is to be recognized that trocars are also known that do not include a spring-loaded tubular element, and that such trocars may also be improved according to the present invention.

After entry into the body cavity, the subassembly which comprises obturator assembly 14 is removed from cannula assembly 12 and cannula 26 remains extended through the body wall and into the body cavity. Cannula 26 thus provides a port of entry for accessory instrumentation. Cannulas for use in endoscopic procedures are typically fabricated from stainless steel or a radiolucent material, e.g., fiberglass. Radiolucent cannulas are preferred where the surgeon anticipates internal imaging, e.g., x-ray imaging of a radiopaque, dye-injected cystic duct, known as a cholangiogram. The materials used to fabricate radiolucent cannulas are substantially dielectric and they are not therefore capable of dissipating electrical energy induced thereon, e.g., when a unipolar cautery is operated therewithin.

According to the present invention, dielectric tubular members adapted to provide endoscopic access for electrical instrumentation, e.g., unipolar electrocautery devices, are provided with conductive means to facilitate conveyance of electrical energy to a grounding region. By dielectric material is meant a material which does not permit transfer of an electrical current at a rate and to a degree which will effectively dissipate an electrical charge and thereby obviate the danger of tissue burn through contact therewith. Fiberglass is an example of such a dielectric material.

Referring again to FIGS. 1 and 2, cannula 26 is fabricated from a dielectric material, and is provided with an electrically conductive wire 34 which extends along the longitudinal axis thereof. Wire 34 provides a means for collecting and transferring electrical energy conveyed and/or induced on or in cannula 26. As shown, wire 34 extends substantially linearly along the length and at the outer surface of cannula 26. However, wire 34 may also be helically wound, oriented in a random pattern, or a variety of other configurations.

Wire 34 connects with circumferential band 36 located toward the proximal end of cannula 26. Band 36 provides a means for grounding cannula assembly 12, and particularly cannula 26, preferably through contact with the body wall of the patient. Band 36 is sized and dimensioned to provide a relatively large area for contact with the body wall, thereby minimizing the current density at any given contact point along band 36 and reducing the likelihood of localized burns as grounding is accomplished. Alternatively, band 36 may be positioned on cannula assembly 12 so as to be outside the patient's body when cannula 26 is extended into the body cavity, and external grounding means may be secured to band 36.

Band 36 may be fixedly secured to cannula 26, or longitudinally movable along the exterior of cannula 26. In instances where band 36 is longitudinally movable, a locking screw 38 may be provided to secure band 36 in a desired position. Regardless of the longitudinal positioning of band 36, wire 34 is adapted to transfer electrical energy thereto in a continuous, uninterrupted fashion.

In use, cannula assembly 12 provides a port of entry for accessory instrumentation by way of cannula 26 extending into a body cavity. Band 36 is typically positioned so as to be in contact with the body wall and may optionally include a gripping mechanism, e.g., external threading, for maintaining cannula 26 in a fixed position relative to the body wall, despite manipulation of accessory instrumentation therethrough. When a surgeon introduces an accessory instrument with electrocautery capability through cannula 26, whether unipolar or bipolar, and energizes that instrument, an electrical charge may be induced in or on cannula 26. However, any risk of burn injury to internal organs or tissue through contact with cannula 26 is obviated through the transfer of such electrical energy along wire 34 to band 36. Through the uninterrupted contact of band 36 with the body wall (or an external grounding mechanism), safe and effective grounding of cannula 26 is achieved.

Figure 3:
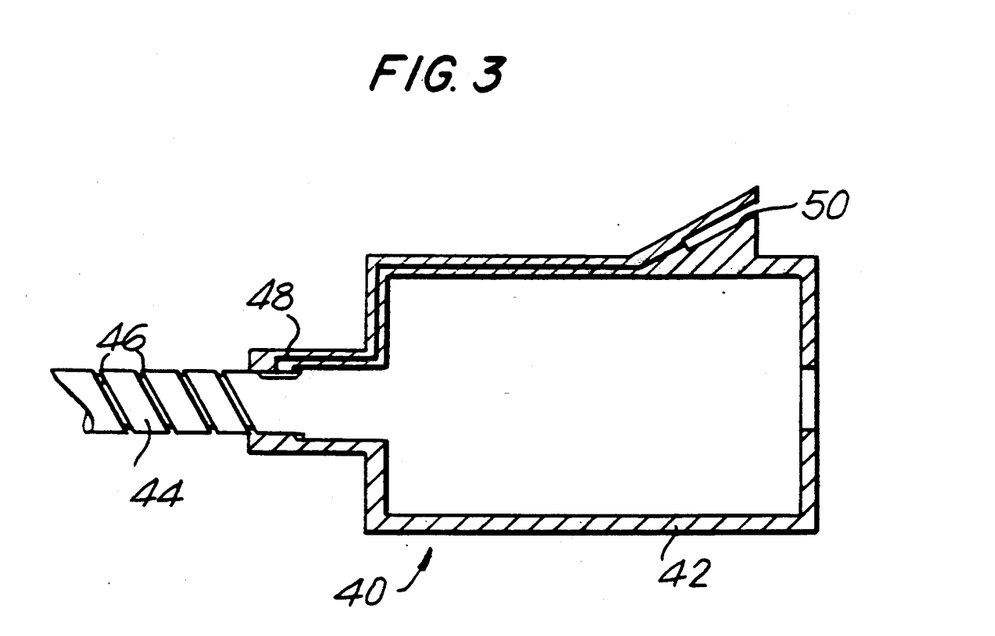
FIG. 3 is a side view, partially in section, of an alternative cannula assembly.

An alternate embodiment is shown in FIG. 3. Cannula assembly 40 includes a cannula housing 42 and cannula 44. An electrically conductive ink 46 is applied to the exterior of cannula 44 in a substantially helical pattern. At the proximal end of cannula 44, conductive ink 46 electrically communicates with wire 48 which is mounted within cannula housing 42. Wire 48 is connected at its opposite end to electrical fitting 50 which is adapted to receive a grounding wire (not shown). The electrical circuitry of conductive ink 46, wire 48 and fitting 50 provides a means for grounding cannula assembly 40, and particularly cannula 44, external to a patient's body.

In a further embodiment of the present invention, an accessory device which is adapted to be associated with a cannula assembly is provided. For example, the accessory device may take the form of a gripping device for use in securing and maintaining the position of cannula assembly with respect to a patient's body wall.

Figure 4:
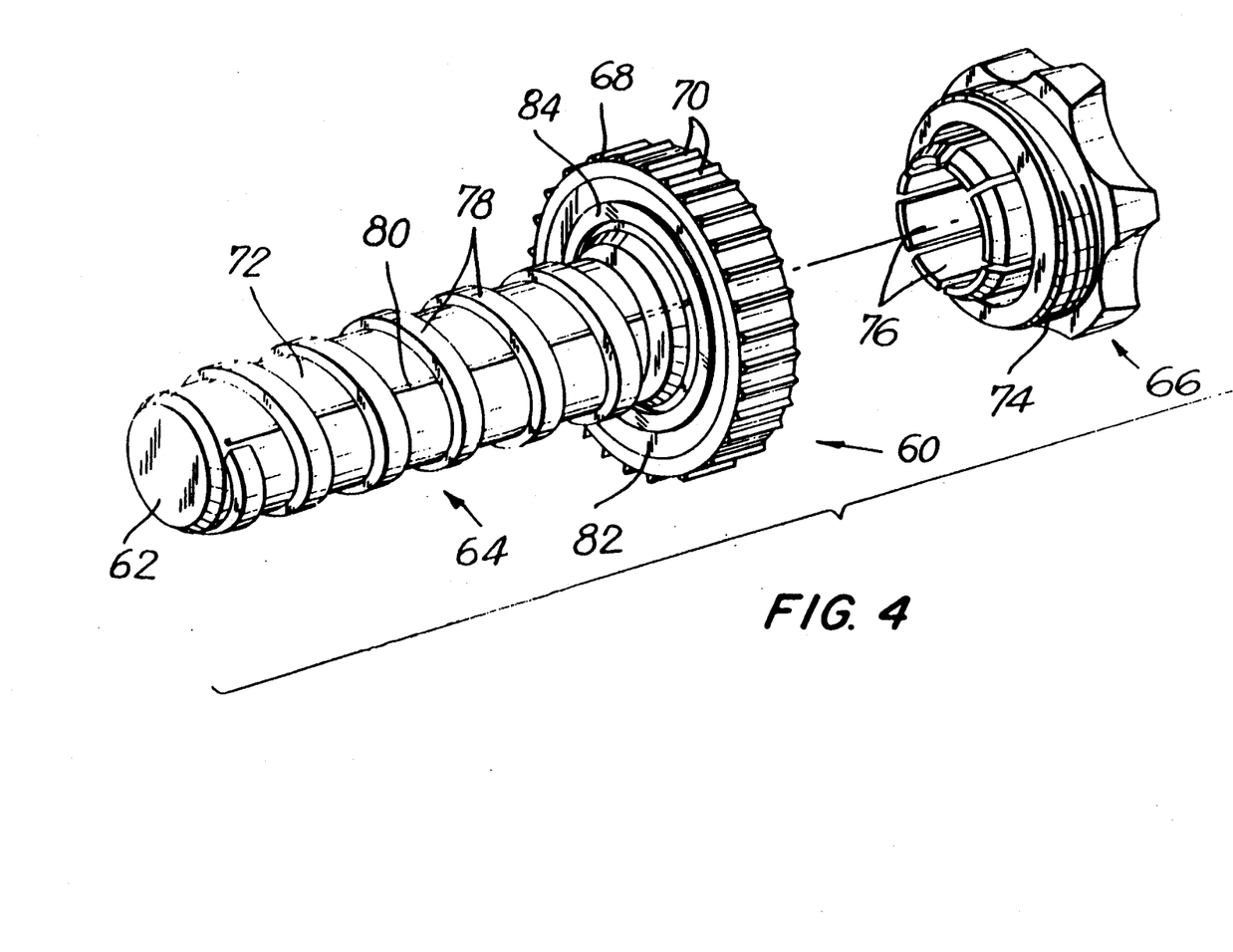
FIG. 4 is a side perspective view of a surgical accessory of the present invention.
Figure 5:
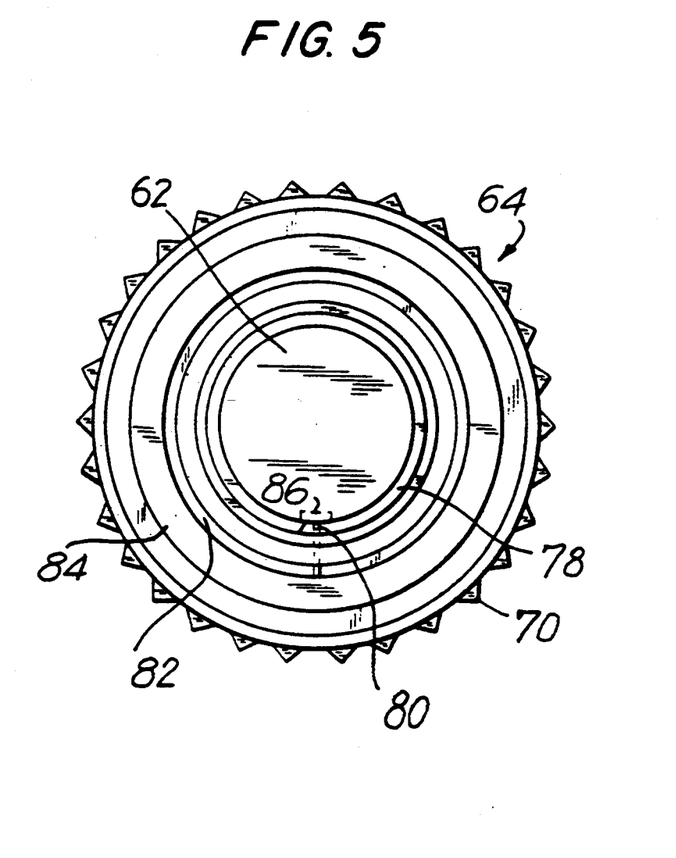
FIG. 5 is a front view of the surgical accessory of FIG. 4.

Referring to FIGS. 4 and 5, accessory device 60 includes an outer housing 64 and an inner housing 66 which have axially aligned apertures to receive a cannula of the type shown in FIGS. 1-3. Outer housing 64 is generally cylindrical with a central aperture 62 and includes a gripping portion 68 supporting gripping projections 70. Outer housing 64 also has an inwardly facing threaded section (not shown) to engage threaded section 74 of inner housing 66. A number of longitudinally extending gripping fingers 76 for frictionally gripping a cannula are provided as part of inner housing 66.

Outer housing 64 includes an integral, distally extending sleeve 72 for surrounding a cannula. Sleeve 72 includes radially projecting ribs 78 which are shown in FIG. 4 as a helical coil extending radially from the outer surface of sleeve 72. An electrically conductive wire 80 passes longitudinally along sleeve 72, connecting at its distal end with inwardly directed contact surface 86 and at its proximal end with distally directed grounding band 84 on forward face 82 of gripping portion 68. Contact surface 86 is adapted to electrically communicate with a cannula when accessory device 60 is mounted thereon. Grounding band 84 is adapted to transfer electrical energy to the body wall of the patient or to an external grounding mechanism, depending on the positioning of the cannula assembly and/or accessory device 60 with respect to the body wall. The relatively large surface area of grounding band 84 minimizes the current density at any given point thereon as grounding takes place, thereby reducing the likelihood of localized burns as grounding is accomplished.

Accessory device 60 acts to dissipate electrical energy induced or transferred to a cannula, regardless of the material from which the cannula is fabricated. In cases where the cannula is fabricated from stainless steel, electrical energy will easily pass along the cannula, through contact surface 86 and wire 80, to grounding band 84. However, in cases where the cannula is fabricated from a dielectric material, e.g., fiberglass, it is preferred that the cannula include energy conductive means of the type described above with respect to cannula 26 in FIGS. 1 and 2.

With the exception of wire 80, contact surface 86 and grounding band 84, accessory device 60 is typically constructed, such as by molding, of glass filled acetal or polycarbonate. One appropriate acetal material is available from LNP Division of ICI America Inc. under the trade specification KFL 4023. A suitable polycarbonate material is available from General Electric Company under the trade name LEXAN.

In use, accessory instrument 60 is positioned on a cannula with inner housing 66 and outer housing 64 loosely engaged. Once located in the desired position on the cannula, inner and outer housing 66, 64 are rotatably threaded together so as to tighten gripping fingers 76 into engagement with the cannula. After penetration of the trocar through the body wall, sleeve 72 is brought into engagement therewith. Sleeve 72 may then be inserted into the incision by straight lateral force or by turning the cannula assembly to effectively "screw" sleeve 72 and helical ribs 78 into the body wall. Once inserted, the body wall surrounds sleeve 72 and extends into the recesses between ribs 78. The body wall is brought into engagement with and thereby acts to ground electrical energy from grounding band 84.

Figure 6:
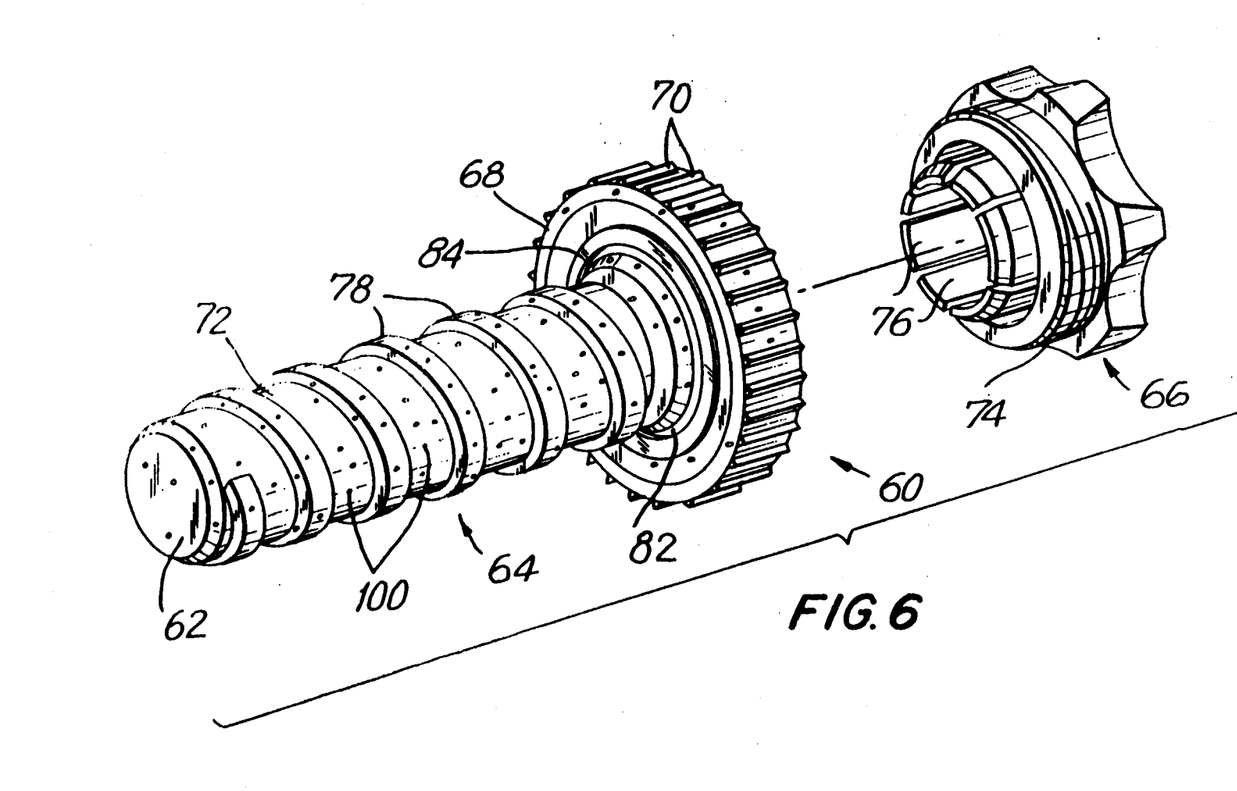
FIG. 6 is a side perspective view of an alternative surgical accessory of the invention.

In a further embodiment of the invention, wire 34 (first embodiment) or wire 74 (second embodiment) may be replaced in whole or in part by electrically conductive particles or materials. Thus, as shown in FIG. 6, electrically conductive particles 100 are interspersed within outer housing 64 and communicate electrically with grounding band 84. Particles 100 may be metallic or non-metallic, e.g., carbon fibers, and are included in an amount effective to transfer energy through accessory device 60 at a rate sufficient to obviate the risk of internal organ burns. For example, particles 100 may constitute from about 2 to 15% by weight of a cannula or accessory device, and may be randomly dispersed, oriented in a fixed pattern, or in fibrous form within the subject device.

Another accessory device in accordance with the preferred embodiment of the subject invention is illustrated in FIG. 6 and is designated generally by reference numeral 200. Accessory device 200 is substantially similar to accessory device 60, described hereinabove, with the exception that, accessory device 200 is not provided with the electrically conductive wire 80. However, accessory device 200 is provided with an electrical conductive coating 210 which facilitates the conduction and dissipation of induced electrical energy via the grounding band 84.

Figure 7:
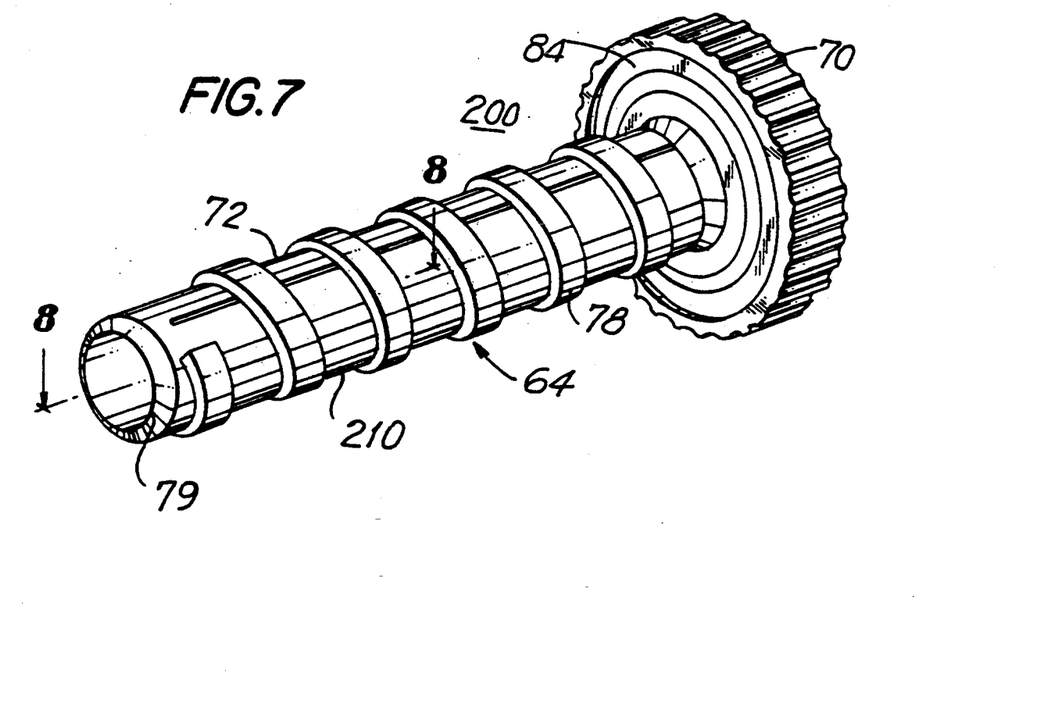
FIG. 7 is a side perspective view of a surgical accessory provided with an electrical conductive coating.

Referring to FIG. 7, the exterior surface 73 of the distally extending sleeve 72 of the outer housing 64 is preferably provided with an electrical conductive coating 210, such that the electrical conductive coating 210 is in electrical communication with the grounding band 84. Therefore, induced electrical charge which accumulates or is transferred to sleeve 72 is conducted to the grounding band 84, whereafter the induced electrical charge is dissipated either into the body wall of the patient or to an external grounding mechanism.

Figure 8:
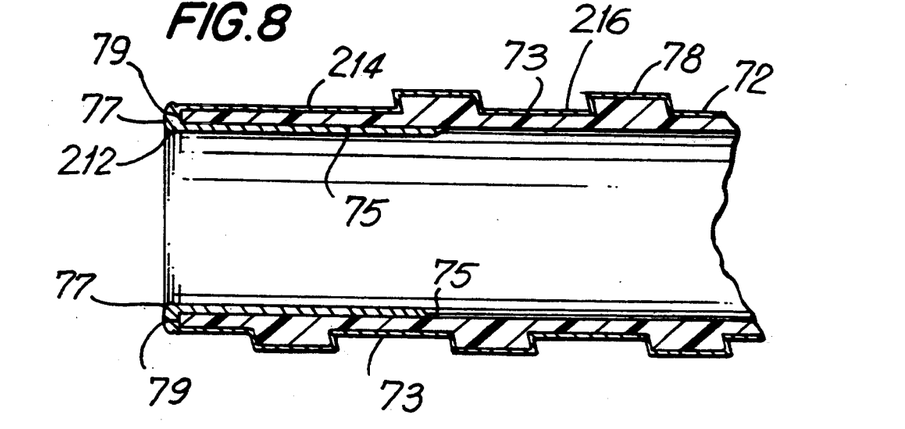
FIG. 8 is a cross-sectional view of the surgical accessory taken along line 8—8 of FIG. 7.

Turning to FIGS. 7 and 8, the electrical conductive coating 210 of the accessory device 200 consists of copper 212, nickel 214 and chrome 216. In applying the electrical conductive coating 210 to the sleeve 72, first, a layer of copper 212 is electrolessly applied to the exterior surface 73 of the sleeve 72. Electroless plating is the preferred method of adhesion because electroless plating enables controlled autocatalytic deposition of a continuous film by the interaction which results from a solution consisting of a metal salt and a chemical reducing agent. A major advantage of electroless solutions is the ability to provide conductive metallic films on nonconductor surfaces, e.g., the sleeve 72. For a more detailed description of electroless plating, See Kirk-Othmer, *Encyclopedia of Chemical Technology*, 3rd edition, Vol. 8, pp. 738–749, which is incorporated herein by reference. In particular, the layer of copper 212 electrolessly plated to the sleeve should preferably be less than 0.0001" thick. Thereafter, a layer of Nickel 214 is electroplated to the electroless plated layer of copper 212. Preferably, the electroplated copper should be between 0.0003 and 0.0005 inches thick. Lastly, a layer of chrome 216, preferably between 20 and 40 micro inches thick is electroplated to the already electroplated layer of copper 214. Chrome 216 is chosen as the preferred outer layer of the electrical conductive coating 210 because of its bio-acceptability properties.

In a preferred embodiment, electrical conductive coating 210 extends around the distal end 79 of sleeve 72 and onto the interior face 75 thereof. Electrical conductive coating 210 on interior face 75 comprises the same materials, is formed in the same way and has the same thickness, as described hereinabove. A rounded region 77 of increased thickness relative to the remainder of coating 210 is generally formed in the region of distal end 79. This rounded region 77 improves the intregity of coating 210 and minimizes the opportunity for trauma associated with tissue contact with distal end 79 of sleeve 72. Coating 72 on the interior face 75 facilitates electrical communication between sleeve 72 and a cannula to which it is mounted, thereby permitting ready transfer of electrical charge and/or current from the cannula to coating 210 for subsequent dissipation, as discussed above.

In use, the electrical conductive coating 200 conducts induced electrical energy along the longitudinal axis of the sleeve 72 to the grounding band 84, wherein the induced electrical energy is dissipated into either the body wall of the patient or to an external grounding mechanism.

While the above description contains many specific details, these details should not be construed as limitations on the scope of the invention, but merely as examples of preferred embodiments thereof. Those skilled in the an will envision many other possible variations that are within the scope and spirit of the invention as defined by the claims appended hereto.

We claim:
1. In combination:
 a) rigid cannula member defining a longitudinal bore for reception of an electrical charge-inducing instrument; and
 b) an accessory surgical device including;
  i) a housing having a gripping portion at a first end, said housing being fabricated from a substantially dielectric material having an exterior and interior surface portion and including structure for mounting said interior surface portion of said housing to an exterior surface portion of said rigid cannula member;
  ii) electrical conductive means disposed on said housing for conducting an induced electrical charge longitudinally along said housing; and
  iii) energy dissipation means disposed on said gripping portion communicating electrically with said electrical conductive means, said energy dissipation means permitting grounding of said housing.

2. The combination as recited in claim 1, wherein said electrical conductive means is a coating selected from the group consisting of copper, nickel and chrome.

3. The combination as recited in claim 1, wherein said structure for mounting said housing to said rigid cannula member includes a plurality of longitudinally extending gripping fingers provided in an interior surface of said housing.

4. The combination as recited in claim 1, wherein said electrical conductive means is a wire extending along said housing.

5. The combination as recited in claim 1, wherein said housing defines an interior surface, an exterior surface and a distal end, and said electrical conductive means is in electrical communication with said interior and exterior surfaces and said distal end.

6. The combination as recited in claim 5, wherein said electrical conductive means is a coating having increased thickness at said distal end of said housing.

7. The combination as recited in claim 1, wherein said accessory device is a tissue gripping device, and said housing is adapted to be mounted to the exterior of said rigid cannula member.

8. The combination as recited in claim 7, wherein said rigid cannula member is fixedly secured to a cannula housing and said tissue gripping device housing is integrally connected to said cannula housing.

9. The combination as recited in claim 7, wherein said tissue gripping device includes engaging means for engaging a body wall of a patient to retain said rigid cannula member in position relative to said body wall.

10. The combination as recited in claim 9, wherein said engaging means comprises a helical gripping projection extending radially outward from said housing.

11. In combination:
 a) rigid cannula member defining a longitudinal bore for reception of an electrical charge-inducing instrument; and
 b) an accessory surgical device including:
  (i) an elongated housing defining a bore therethrough dimensioned and configured for reception of said rigid cannula member, said housing including:
   (a) an outer housing having a gripping portion and an elongated sleeve extending distally from said gripping portion, said elongated sleeve having an interior and exterior surface; and
   (b) an inner housing engaged in axial alignment with said outer housing, said inner housing having an interior and exterior surface and including structure for mounting said interior surface of said inner housing to said exterior of said rigid cannula member;
  ii) an energy dissipation means in electrical communication with said gripping portion for transferring electrical energy to a grounding surface; and
  iii) an electrical conductive coating adhered to the interior and to the exterior surface of said elongated sleeve and in electrical communication with said energy dissipation means of said gripping portion for conducting an induced electrical charge longitudinally along said elongated sleeve to said gripping portion.

12. The combination as recited in claim 11, wherein said electrical conductive coating is selected from the group consisting of copper, nickel and chrome.

13. The combination as recited in claim 11, wherein said electrical conductive coating on said interior surface of said elongated sleeve is in electrical communication with said exterior of said rigid cannula member.

14. The combination as recited in claim 11, wherein said structure for mounting said housing to said rigid cannula member includes a plurality of longitudinally extending gripping fingers provided in said interior surface of said inner housing.

15. The combination as recited in claim 11, wherein said inner housing is threadingly engaged to said outer housing.

16. The combination as recited in claim 15, wherein said inner housing is provided with a threaded section configured to threadingly engage an inwardly facing threaded section provided in said outer housing.

17. A method for dissipating induced electrical energy from a rigid cannula member comprising:
   (a) providing a housing having a gripping portion at a first end, said housing including mounting structure for mounting said housing to said rigid cannula member, said housing defining a longitudinal axis, said housing being fabricated from a dielectric material and comprising (i) electrical conductive means disposed on said housing for conducting electrical energy along said longitudinal axis and (ii) energy dissipation means disposed on said gripping portion communicating electrically with said electrical conductive means;
   (b) mounting said housing to said rigid cannula member such that said rigid cannula member is engaged by said mounting structure of said housing and is in electrical communication with said electric conductive means, and introducing said rigid cannula member through a body wall of a patient;
   (c) introducing an electrical charge-inducing instrument through said rigid cannula member and energizing said electrical charge inducing element therewithin; and
   (d) grounding said cannula member and said housing through electrical communication between said energy dissipation means and a grounding medium.

18. The method according to claim 17, wherein said grounding step comprises placing said gripping portion and said energy dissipation means into contact with a surface of said body wall of said patient.

* * * * *